US005747290A

United States Patent [19]
Emtage et al.

[11] Patent Number: 5,747,290
[45] Date of Patent: May 5, 1998

[54] PROCESS FOR THE PRODUCTION OF RECOMBINANT POLYPEPTIDES

[75] Inventors: John Spencer Emtage, Marlow, England; Malcolm Roy Brandon, Ivanhoe East Melbourne, Australia

[73] Assignee: Southern Cross Biotech Party, Ltd., Victoria, Australia

[21] Appl. No.: 468,824

[22] Filed: Jun. 6, 1995

Related U.S. Application Data

[63] Continuation of Ser. No. 134,946, Oct. 12, 1993, abandoned, which is a continuation of Ser. No. 984,244, Dec. 1, 1992, abandoned, which is a continuation of Ser. No. 717,179, Jun. 18, 1991, abandoned, which is a division of Ser. No. 480,051, Feb. 14, 1990, abandoned, which is a continuation of Ser. No. 148,519, Jan. 26, 1988, abandoned.

[30] Foreign Application Priority Data

Jan. 28, 1987 [GB] United Kingdom ............... 8701848

[51] Int. Cl.⁶ ............... C12P 21/02; C07H 21/04; C12N 15/70
[52] U.S. Cl. ............... 435/69.4; 435/320.1; 536/23.51
[58] Field of Search ............... 435/69.4, 69.1, 435/320.1; 536/23.51

[56] References Cited

U.S. PATENT DOCUMENTS

| 4,582,800 | 4/1986 | Crowl | 435/69.51 |
| 4,705,848 | 11/1987 | Yang et al. | 530/399 |

FOREIGN PATENT DOCUMENTS

| 0104920 | 4/1984 | European Pat. Off. | C12N 15/00 |
| 0111389 | 6/1984 | European Pat. Off. | |
| 0147178 | 7/1985 | European Pat. Off. | |

OTHER PUBLICATIONS

Shepard et al., DNA 1(2), pp. 125–131 (1982), "Increased Synthesis in *E.coli* of Fibroblast and Leukocyte Interferons through Alterations in Ribsome Binding . . . ".
Itoh et al., DNA 3(2), pp. 157–165 (1984), Efficient Expression in *Escherichia coli* of a Mature and Modified Human Interferon-$\beta_1$.
Windass et al., NAR 10(21), pp. 6639–6657 (1982), "The Construction of a Synthetic *Escherichia coli* trp promoter and its use in the Expression of Synthetic . . . Gene".
DeBoer et al., DNA 2(3), pp. 231–235 (1983), "Portable Shine–Dalgarno Regions: A System for a Systematic Study of Defined Alterations of Nucleotide Sequences . . . Sites".
Scherer et al. (1980), Nucl. Acids Res. 8(17): 3895–3907.
Roberts et al. (1979), Proc. Natl. Acad. Sci USA 76(2): 760–764.
Lewin, Genes (John Wiley & Sons, New York, 1983), pp. 154–157.
Machlin (1972), J. Animal Sci 35(4): 794–800.
Yarranton et al. (1984), Gene 28: 293–300.

*Primary Examiner*—Nancy Degen
*Attorney, Agent, or Firm*—Spencer & Frank

[57] ABSTRACT

A process for producing recombinant polypeptides having porcine growth hormone activity, by culturing unicellular organisms containing synthetic DNA sequences coding for such polypeptides and expressing and recovering the polypeptides is described. The recombinant polypeptides may be used in animals in veterinary compositions as effective substitutes for natually derived porcine growth hormone. Recombinant DNA processes for the preparation of the unicellular organisms are also described.

9 Claims, 7 Drawing Sheets

Pst1  Apa1  BssHII  Apa1  AccI  SmaI  PvuII  Pst1
Partial restriction map of pGH cDNA
(not to scale)
FIG. 1
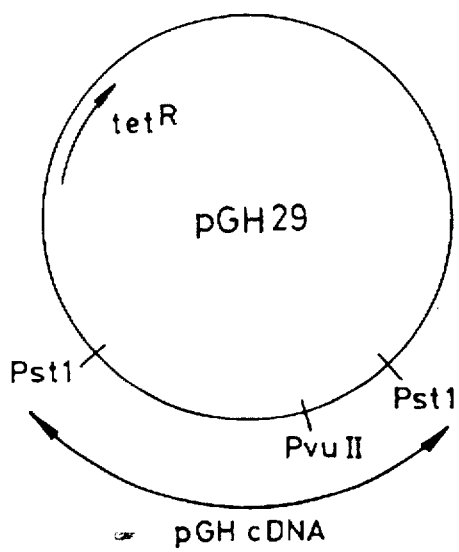
FIG. 2
pGH29 (pGH cDNA in pBR322)
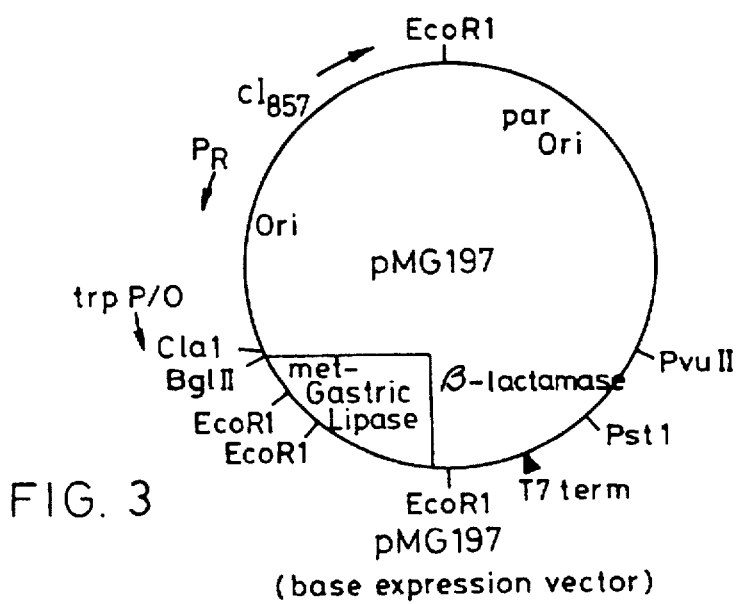
FIG. 3
pMG197
(base expression vector)

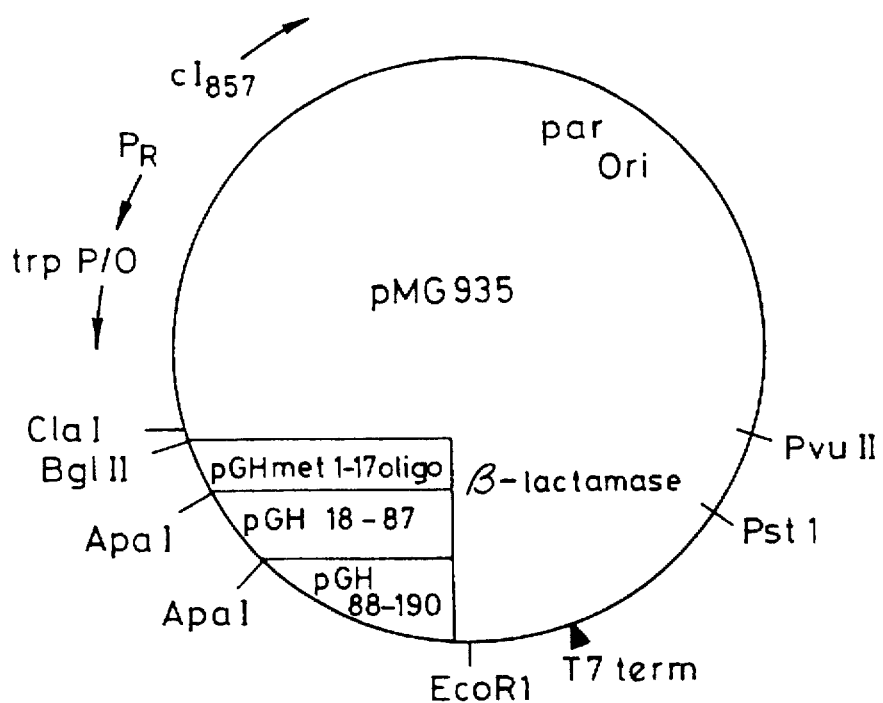
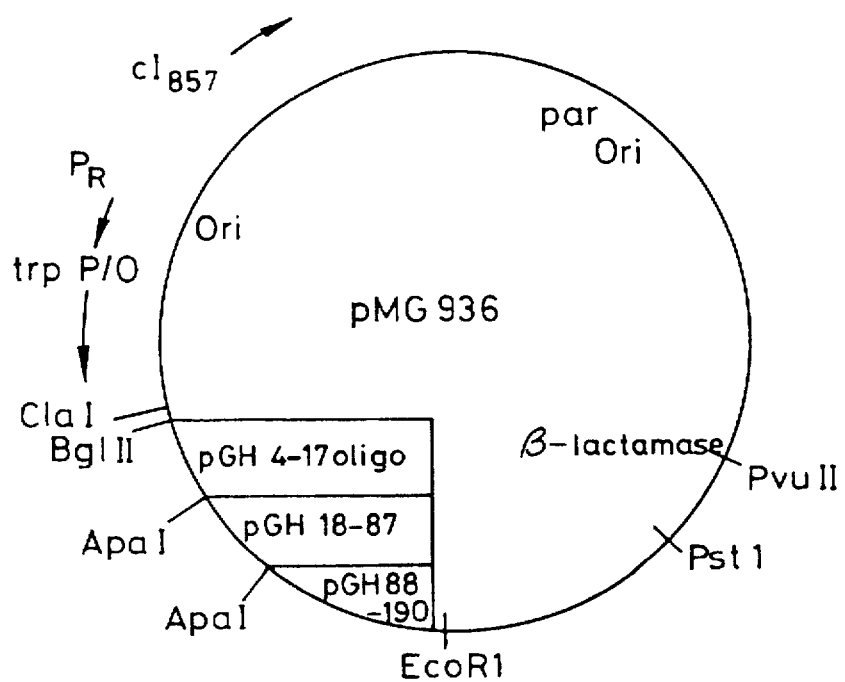
FIG. 4

```
                                              12 bases missing from
                                              pMG 936 construction
                  Hpa I                       /------\         M  F  P  P  A  M  P  L  S  S  L  F  A  N  A  V  L  R  A  Q
AATTAATCATCGAACTAGTAGTTAACTAGTACGCAAGTTCACGTAAAAAGGGTATCGATAGATCTAGTTTCCAGCTATGCCACTTCTCTGTTCCTAACGCTGTTCTTCGGGCCCAGC
         10        20        30        40        50        60        70        80        90       100       110       120

H  L  H  Q  L  A  A  D  T  Y  K  E  F  E  R  A  Y  I  P  E  G  Q  R  Y  S  I  Q  N  A  Q  A  A  F  C  F  S  E  T  I  P
ACCTGCACCAACTGGCTGCCGACACCTACAAGGAGTTTGAGCGGGCCTACATCCCCGAGGAGCAGAGGTACTCCATCCAGAACGCCCAGGCTGCCTTCTGCTTCTCGGAGACCATCCCGG
        130       140       150       160       170       180       190       200       210       220       230       240

Apa I
 A  P  T  G  K  D  E  A  Q  Q  R  S  D  V  E  L  L  R  F  S  L  L  L  I  Q  S  W  L  G  P  V  Q  F  L  S  R  V  F  T  N
CCCCCACGGGCAAGGACGAGGCCCAGCAGCGCTCCGACGTGGAGCTGCTCCGCTTCTCTCTGCTCCTCATCCAGAGTTGGCTGGGCCCCGTCCAGTTCCTCAGCAGGGTCTTCACCAACA
        250       260       270       280       290       300       310       320       330       340       350       360

Sma I
 S  L  V  F  G  T  S  D  R  V  Y  E  K  L  K  D  L  E  E  G  I  Q  A  L  M  R  E  L  E  D  G  S  P  R  A  G  G  Q  I  L  K
GCCTTGGTGTTTGGAACCTCAGACCGGGTCTACGAGAAGCTGAAGGACCTGGAGGAGGGCATCCAGGCCCTGATGCGGGAGCTGGAGGATGGCAGCCCCGGGGCAGGACAGATCCTCAAGC
        370       380       390       400       410       420       430       440   ▲   450       460       470       480
                                                                                     A

Q  T  Y  D  K  F  D  T  N  L  R  S  D  D  A  L  L  K  N  Y  G  L  L  S  C  F  K  K  D  L  H  K  A  E  T  Y  L  R  V  M
AAACCTACGACAAATTTGACACAAACCTGCGCAGTGATGACGCCCTGCTCAAGAACTACGGGCTGCTGTCCTGCTTCAAGAAGGACCTGCACAAGGCTGAGACATACCTGCGGGTCATGA
        490       500       510       520       530       540       550       560       570       580       590       600

K  C  R  R  F  V  E  S  S  C  A  F
AGTGTCGCCGCTTCGTGGAGAGCAGCTGCGCCTTCTAGTTGCTGTGGGCCATTCTCTGTTGCCCCTCCCCAGTACCTCCCCTTGACCCTGAAAAATGCCACCCAATGCCTGCTTCCTTTCCTA
        610       620       630       640       650       660       670       680       690       700       710       720

ATTAAACCAGTTTCATCGTAAAAAAAAAAAAAA
        730       740       750
```

FIG. 6

OPTIMISATION OF EXPRESSION BY SHORTENING SD-ATG DISTANCE

| Treatment | Bases Removed | New SD-ATG Distance |
|---|---|---|
| Cla 1, S1, | 5,6, | 12 |
| Bgl 2, S1, | 10,11,12,13 | 10 |
| Cla 1, Klenow + Bgl 2, Klenow | 7,8,9 | 11 |
| Cla 1, Klenow + Bgl 2, S1 | 7,8,9,10,11,12,13 | 7 |
| Cla 1, S1 + Bgl 2, Klenow | 5,6,7,8,9 | 9 |
| Cla 1, S1 + Bgl 2, S1 | 5,6,7,8,9,10,11,12 | 5 |

MODIFIED pGH CONSTRUCTS (met 1 to 190)

| Treatment | SD to ATG distance | | Plasmid |
| --- | --- | --- | --- |
| | Expected (bases removed) | Observed (bases removed) | |
| None | 14 | 14 | pMG939 |
| Cla1, S1 | 12 (5,6) | 11 (5,6,7) | pMG939-12 |
| Cla1, Pol1) + ) Bgl2, Pol1) | 11 (7,8,9) | 11 (7,8,9) | pMG939-11 |
| Bgl2  S1 | 10 (10,11,12,13) | 8 (10,11,12,13,14 + 9 or 15) | pMG939-10 |
| Cla1, S1 ) + ) Bgl2, Pol1) | 9 (5,6,7,8,9) | 9 (5,6,7,8,9) | pMG939-09 |
| Cla1, Pol1) + ) Bgl2 S1 ) | 7 (7,8,9,10,11, 12,13) | Not Sequenced | pMG939-07 |
| Cla1, S1 ) + ) Bgl2, S1 ) | 5 (5,6,7,8,9,10 11,12,13) | Not Sequenced | pMG939-05 |

FIG. 8

MODIFIED pGH CONSTRUCTS (4 to 190)

| Treatment | SD to ATG distance | | Plasmid |
| --- | --- | --- | --- |
| | Expected (bases removed)* | Observed (base removed)* | |
| None | 14 | 14 | pMG940 |
| Cla1, S1 | 12<br>(5,6) | 12<br>(5,6) | pMG940-12 |
| Cla1, Pol1)<br>+ )<br>Bgl2, Pol1) | 11<br>(7,8,9) | Not<br>Sequenced | pMG940-11 |
| Bgl2 S1 | 10<br>(10,11,12,13) | 8<br>(10,11,12,13,14<br>+ 9 or 15) | pMG040-10 |
| Cla1, S1 )<br>+ )<br>Bgl2, Pol1) | 9<br>(5,6,7,8,9) | 9<br>(5,6,7,8,9) | pMG940-9 |
| Cla1, Pol1)<br>+ )<br>Bgl2 S1 ) | 7<br>(7,8,9,10,<br>11,12,13) | Not<br>Sequenced | pMG940-07 |
| Cla1, S1 )<br>+ )<br>Bgl2, S1 ) | 5<br>(5,6,7,8,9,<br>10,11,12,13) | Not<br>Sequenced | pMG940-05 |

FIG. 9

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x ) PUBLICATION INFORMATION:
        ( H ) DOCUMENT NUMBER: GB 8701848
        ( I ) FILING DATE: 28-JAN-1987

( x i ) SEQUENCE DESCRIPTION: SEQ ID NO:1:

```
GATCTATGTT TCCAGCTATG CCACTTTCTT CTCTGTTCGC TAACGCTGTT CTTCGGGCC        59
```

( 2 ) INFORMATION FOR SEQ ID NO:2:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x ) PUBLICATION INFORMATION:
        ( H ) DOCUMENT NUMBER: GB 8701848
        ( I ) FILING DATE: 28-JAN-1987

( x i ) SEQUENCE DESCRIPTION: SEQ ID NO:2:

```
CGAAGAACAG CGTTAGCGAA CAGAGAAGAA AGTGGCATAG CTGGAAACAT A        51
```

( 2 ) INFORMATION FOR SEQ ID NO:3:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x ) PUBLICATION INFORMATION:

( H ) DOCUMENT NUMBER: GB 8701848
( I ) FILING DATE: 28-JAN-1987

( x i ) SEQUENCE DESCRIPTION: SEQ ID NO:3:

GATCTATGCC ACTTTCTTCT CTGTTCGCTA ACGCTGTTCT TCGGGCC    47

( 2 ) INFORMATION FOR SEQ ID NO:4:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: YES ( x ) PUBLICATION INFORMATION:
        ( H ) DOCUMENT NUMBER: GB 8701848
        ( I ) FILING DATE: 28-JAN-1987

( x i ) SEQUENCE DESCRIPTION: SEQ ID NO:4:

GGAAGAACAG CGTTAGCGAA CAGAGAAGAA AGTGGCATA    39

( 2 ) INFORMATION FOR SEQ ID NO:5:

( i ) SEQUENCE CHARACTERISTICS:
        ( A ) LENGTH: 755 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 63..635

( x ) PUBLICATION INFORMATION:
        ( H ) DOCUMENT NUMBER: GB 8701848
        ( I ) FILING DATE: 28-JAN-1987

( x i ) SEQUENCE DESCRIPTION: SEQ ID NO:5:

```
AATTAATCAT CGAACTAGTT AACTAGTACG CAAGTTCACG TAAAAAGGGT ATCGATAGAT         60

CT ATG TTT CCA GCT ATG CCA CTT TCT TCT CTG TTC GCT AAC GCT GTT          107
   Met Phe Pro Ala Met Pro Leu Ser Ser Leu Phe Ala Asn Ala Val
   1               5                   10                  15

CTT CGG GCC CAG CAC CTG CAC CAA CTG GCT GCC GAC ACC TAC AAG GAG          155
Leu Arg Ala Gln His Leu His Gln Leu Ala Ala Asp Thr Tyr Lys Glu
            20                  25                  30

TTT GAG CGC GCC TAC ATC CCG GAG GGA CAG AGG TAC TCC ATC CAG AAC          203
Phe Glu Arg Ala Tyr Ile Pro Glu Gly Gln Arg Tyr Ser Ile Gln Asn
                35                  40                  45

GCC CAG GCT GCC TTC TGC TTC TCG GAG ACC ATC CCG GCC CCC ACG GGC          251
Ala Gln Ala Ala Phe Cys Phe Ser Glu Thr Ile Pro Ala Pro Thr Gly
            50                  55                  60

AAG GAC GAG GCC CAG CAG AGA TCG GAC GTG GAG CTG CTG CGC TTC TCG          299
Lys Asp Glu Ala Gln Gln Arg Ser Asp Val Glu Leu Leu Arg Phe Ser
    65                  70                  75

CTG CTG CTC ATC CAG TCG TGG CTC GGG CCC GTG CAG TTC CTC AGC AGG          347
Leu Leu Leu Ile Gln Ser Trp Leu Gly Pro Val Gln Phe Leu Ser Arg
80                  85                  90                  95
```

| | | | | | | | | | | | | | | | | |
|---|---|---|---|---|---|---|---|---|---|---|---|---|---|---|---|---|
| GTC | TTC | ACC | AAC | AGC | CTG | GTG | TTT | GGC | ACC | TCA | GAC | CGC | GTC | TAC | GAG | 395 |
| Val | Phe | Thr | Asn | Ser | Leu | Val | Phe | Gly | Thr | Ser | Asp | Arg | Val | Tyr | Glu | |
| | | | | 100 | | | | | 105 | | | | | 110 | | |
| AAG | CTG | AAG | GAC | CTG | GAG | GAG | GGC | ATC | CAG | GCC | CTG | ATG | CGG | GAG | CTG | 443 |
| Lys | Leu | Lys | Asp | Leu | Glu | Glu | Gly | Ile | Gln | Ala | Leu | Met | Arg | Glu | Leu | |
| | | | 115 | | | | | 120 | | | | | 125 | | | |
| GAG | GAT | GGC | AGC | CCC | CGG | GCA | GGA | CAG | ATC | CTC | AAG | CAA | ACC | TAC | GAC | 491 |
| Glu | Asp | Gly | Ser | Pro | Arg | Ala | Gly | Gln | Ile | Leu | Lys | Gln | Thr | Tyr | Asp | |
| | | 130 | | | | | 135 | | | | | 140 | | | | |
| AAA | TTT | GAC | ACA | AAC | TTG | CGC | AGT | GAT | GAC | GCG | CTG | CTT | AAG | AAC | TAC | 539 |
| Lys | Phe | Asp | Thr | Asn | Leu | Arg | Ser | Asp | Asp | Ala | Leu | Leu | Lys | Asn | Tyr | |
| | 145 | | | | | 150 | | | | | 155 | | | | | |
| GGG | CTG | CTC | TCC | TGC | TTC | AAG | AAG | GAC | CTG | CAC | AAG | GCT | GAG | ACA | TAC | 587 |
| Gly | Leu | Leu | Ser | Cys | Phe | Lys | Lys | Asp | Leu | His | Lys | Ala | Glu | Thr | Tyr | |
| 160 | | | | | 165 | | | | | 170 | | | | | 175 | |
| CTG | CGG | GTC | ATG | AAG | TGT | CGC | CGC | TTC | GTG | GAG | AGC | AGC | TGT | GCC | TTC | 635 |
| Leu | Arg | Val | Met | Lys | Cys | Arg | Arg | Phe | Val | Glu | Ser | Ser | Cys | Ala | Phe | |
| | | | | 180 | | | | | 185 | | | | | 190 | | |

| | | | | | |
|---|---|---|---|---|---|
| TAGTTGCTGG | GCATCTCTGT | TGCCCCTCCC | CAGTACCTCC | CTTGACCCTG | GAAAATGCCA | 695 |
| CCCCAATGCC | TGCTTTCCTT | TCCTAATTAA | ACCAGGTTTC | ATCGTAAAAA | AAAAAAAAA | 755 |

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
        (H) DOCUMENT NUMBER: GB 8701848
        (I) FILING DATE: 28-JAN-1987

(xi) SEQUENCE DESCRIPTION: SEQ ID NO:6:

AAGGGTATCG ATAGATCTAT G        21

(2) INFORMATION FOR SEQ ID NO:7:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (x) PUBLICATION INFORMATION:
        (H) DOCUMENT NUMBER: GB 8701848
        (I) FILING DATE: 28-JAN-1987

(xi) SEQUENCE DESCRIPTION: SEQ ID NO:7:

| | | | | | | | | | | | | | | |
|---|---|---|---|---|---|---|---|---|---|---|---|---|---|---|
| Met | Phe | Pro | Ala | Met | Pro | Leu | Ser | Ser | Leu | Phe | Ala | Asn | Ala | Val | Leu |
| 1 | | | | 5 | | | | | 10 | | | | | 15 | |
| Arg | Ala | Gln | Xaa | Gln | Leu | | | | | | | | | | |
| | | | 20 | | | | | | | | | | | | |

( 2 ) INFORMATION FOR SEQ ID NO:8:

( i ) SEQUENCE CHARACTERISTICS:
       ( A ) LENGTH: 191 amino acids
       ( B ) TYPE: amino acid
       ( D ) TOPOLOGY: linear ( i i ) MOLECULE TYPE: protein ( x i ) SEQUENCE DESCRIPTION: SEQ ID NO:8:

```
Met  Phe  Pro  Ala  Met  Pro  Leu  Ser  Ser  Leu  Phe  Ala  Asn  Ala  Val  Leu
 1              5                        10                       15

Arg  Ala  Gln  His  Leu  His  Gln  Leu  Ala  Ala  Asp  Thr  Tyr  Lys  Glu  Phe
               20                        25                       30

Glu  Arg  Ala  Tyr  Ile  Pro  Glu  Gly  Gln  Arg  Tyr  Ser  Ile  Gln  Asn  Ala
          35                        40                       45

Gln  Ala  Ala  Phe  Cys  Phe  Ser  Glu  Thr  Ile  Pro  Ala  Pro  Thr  Gly  Lys
     50                        55                       60

Asp  Glu  Ala  Gln  Gln  Arg  Ser  Asp  Val  Glu  Leu  Leu  Arg  Phe  Ser  Leu
 65                      70                       75                       80

Leu  Leu  Ile  Gln  Ser  Trp  Leu  Gly  Pro  Val  Gln  Phe  Leu  Ser  Arg  Val
               85                        90                       95

Phe  Thr  Asn  Ser  Leu  Val  Phe  Gly  Thr  Ser  Asp  Arg  Val  Tyr  Glu  Lys
              100                       105                      110

Leu  Lys  Asp  Leu  Glu  Glu  Gly  Ile  Gln  Ala  Leu  Met  Arg  Glu  Leu  Glu
          115                       120                      125

Asp  Gly  Ser  Pro  Arg  Ala  Gly  Gln  Ile  Leu  Lys  Gln  Thr  Tyr  Asp  Lys
     130                       135                      140

Phe  Asp  Thr  Asn  Leu  Arg  Ser  Asp  Asp  Ala  Leu  Leu  Lys  Asn  Tyr  Gly
145                       150                      155                      160

Leu  Leu  Ser  Cys  Phe  Lys  Lys  Asp  Leu  His  Lys  Ala  Glu  Thr  Tyr  Leu
                165                       170                      175

Arg  Val  Met  Lys  Cys  Arg  Arg  Phe  Val  Glu  Ser  Ser  Cys  Ala  Phe
               180                       185                      190
```

PROCESS FOR THE PRODUCTION OF RECOMBINANT POLYPEPTIDES

This application is a continuation, application Ser. No. 08/134,946, filed Oct. 12, 1993, now abandoned, which is a continuation of application Ser. No. 07/984,244 filed Dec. 1, 1992, now abandoned, which is a continuation of application Ser. No. 07/717,179 filed Jun. 18, 1991, now abandoned, which is a division of application Ser. No. 07/480,051 filed Feb. 14, 1990, now abandoned, which is a continuation of application Ser. No. 07/148,519 filed Jan. 26, 1988, now abandoned.

This invention relates to the production of recombinant polypeptides having porcine growth hormone activity by culturing unicellular organisms containing synthetic DNA sequences coding for such polypeptides; to recombinant DNA technology processes for the preparation of such organisms; to specific plasmid vectors; and to veterinary compositions containing specific polypeptides having porcine growth hormone activity.

BACKGROUND OF THE INVENTION

Growth hormone, a polypeptide hormone, is synthesised in the anterior lobe of the pituitary gland as a larger precursor molecule. In nature the precursor molecule is processed by cleavage to yield the biologically active form of the hormone. Growth hormone, well recognized as a general anabolic agent, promotes a myriad of physiological effects throughout the life-cycle. As its name implies, it is a growth promoter responsible for skeletal growth and a potentiator of protein synthesis. Growth hormone also displays insulin-potentiating properties, has weak lactogenic activity and plays a role in lipid metabolism and homeostatic maintenance.

To some degree, growth hormone is species-specific. For example, bovine hormone is inactive in man and monkey, but will elicit effects in rats and goats.

In pig farming, administration of growth hormone promotes weight gain and improves carcass quality, thereby enhancing the feed conversion ratio. Economic projections indicate that by treating pigs with growth hormone, the quality of meat improves in conjunction with the efficiency and costs of production. Unfortunately, the supply of natural porcine pituitary hormone falls short of its demand, and given the limitations imposed by species specificity, other natural homologues can not be used cheaply as substitutes.

The shortfall can be circumvented by utilising recombinant DNA techniques and bacteria to produce analogous polypeptides in accordance with established methodology. However, such approaches have certain inherent deficiencies, one of which is that eukaryotic DNA is generally unsuitable for expression in bacteria because it often contains non-coding regions or introns which interrupt the gene. This phenomenon is not observed in bacterial genomes. Other problems stem from the incompatibility of eukaryotic and prokaryotic regulatory sequences.

Accordingly, it is an object of the present invention to overcome, or at least alleviate, one or more of the difficulties related to the prior art. In particular we have been able to produce, using the processes described hereinafter, relatively large quantities of recombinant polypeptides having good porcine growth hormone activity. The polypeptides have good activity and can be used in vivo as effective substitutes for the natural hormone.

SUMMARY OF THE INVENTION

Thus according to one aspect of the invention we provide a process for the production of a recombinant polypeptide having porcine growth hormone activity which process includes the steps of (1) (a) providing a recombinant plasmid expression vector including a DNA sequence coding for a polypeptide having porcine growth hormone activity and capable of being replicated, transcribed and translated in a unicellular organism, and (b) a unicellular organism;

(2) introducing said recombinant plasmid expression vector into said unicellular organism by a method selected from transformation, transduction, or transfection;

(3) culturing the resulting organism;

(4) expressing the recombinant polypeptide encoded by said DNA sequence; and optionally (5) isolating said polypeptide from the culture.

BRIEF DESCRIPTION OF THE DRAWINGS

FIG. 1 represents a partial restriction map of porcine growth hormone cDNA (not to scale).

FIG. 2 represents plasmid pGH29.

FIG. 3 represents plasmid pMG197.

FIG. 4 represents plasmids pMG935 and pMG936.

FIG. 6 depicts the pGH cDNA insert in plasmid pMG936.

FIGS. 8 and 9 list the combined enzyme treatments for altering the length of the Shine-Dalgarno to ATG sequence in plasmids pMG939 and pMG940 and the expected result.

DESCRIPTION OF THE PREFERRED EMBODIMENTS

Figure 5:
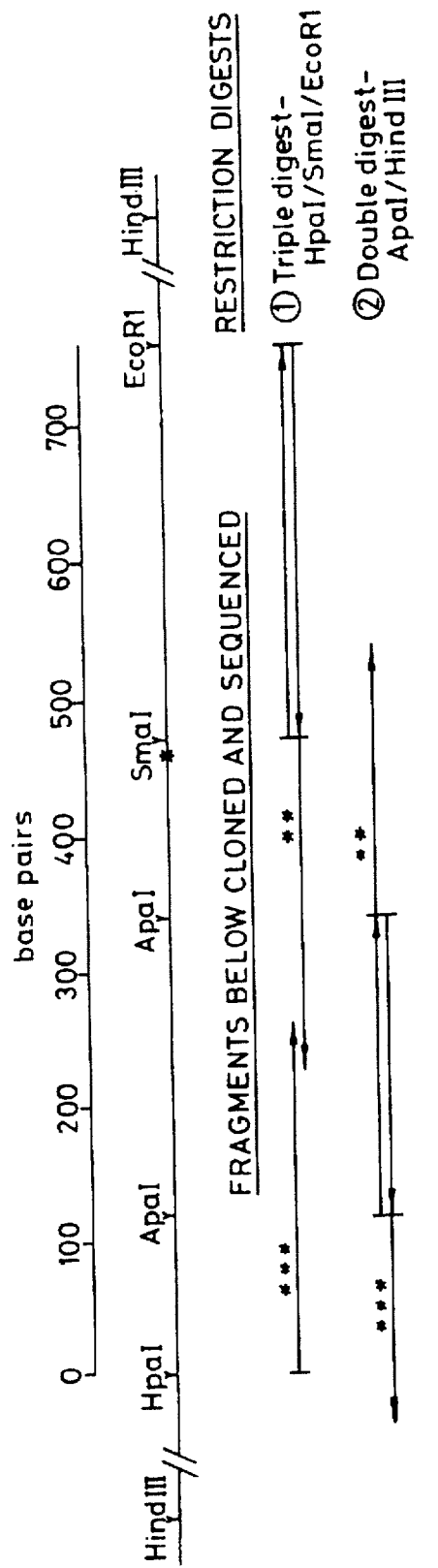
FIG. 5 depicts the strategy for sequencing pGH gene in plasmid pMG936.

In the process according to the invention, the unicellular organism may be a prokaryotic organism, for example a bacterial strain such as a strain of E. coli. The E. coli strain E. coli DH1 has been found to be particularly suitable.

The recombinant plasmid expression vector for use in this aspect of the invention may be any suitable vector prepared using the techniques described below. Particularly useful vectors include pMG935, pMG936, pMG939 and pMG940 as specifically described hereinafter. Such expression vectors form a further aspect of the invention.

The process according to the invention is particularly suitable for preparing recombinant polypeptides pGH(met 1-190) and pGH(4-190) as defined herein.

Steps (1)–(4) of the process according to the invention may be carried out using well-known methodology, for example as described in the Examples hereinafter. Where it is desired to isolate the polypeptide product according to steps (5), conventional procedures may also be used. Thus, after cell disruption, e.g. by cell lysis, the isolation of the polypeptide may be conducted utilising for example chromatography involving ion exchange, affinity or sizing resins, and/or by sedimentation e.g.centrifugation or by other known techniques for the purification of polypeptides.

Where the recombinant polypeptide is expressed as an insoluble aggregate and/or is denatured, solubilisation and/or renaturation may be effected using conventional techniques, for example as described in International Patent Specification WO 83/04418, UK Patent Specification 2138004 and European Patent Specification 226448.

Particularly useful organisms for use in step (3) of the process according to the invention include E. coli strains, especially *E. coli* DH1, containing one of the recombinant plasmid expression vectors pMG935, pMG936, pMG939, and pMG940, and such strains, together with mutants, recombinants and genetically-engineered derivatives thereof form a further aspect of the invention.

Particularly useful recombinant polypeptides we have prepared using the process of the invention include the porcine growth hormone variants pGH(met 1-190) and pGH(4-190). Both recombinant polypeptides have surprisingly good in vivo activity relative to the naturally occurring hormone and may be used in animals, especially pigs, for example to improve carcass quality and/or to promote weight gain. For use in this way pGH(met 1-190) and pGH(4-190) may be administered to the animal in veterinary formulations.

Thus according to a further aspect of the invention we provide a veterinary composition comprising a recombinant polypeptide having porcine growth hormone activity selected from pGH(met 1-190) or pGH(4-190) and the veterinarily acceptable salts thereof together with one or more carriers acceptable for veterinary use.

The term pGH(met 1-190) as used herein is intended to mean a recombinant polypeptide with the amino acid sequence of naturally occurring porcine growth hormone, additionally substituted with a methionine residue at the N-terminus. The term pGH(4-190) is intended to mean a polypeptide with the amino acid sequence of naturally occurring porcine growth hormone except that the first three N-terminal amono acids (Phe-Pro-Ala-) are not present.

Veterinarily acceptable salts of pGH(met 1- 190) and pGH(4-190) include salts of acids or bases, for example inorganic acid salts such as hydrochlorides, or inorganic base salts such as alkali metal, e.g. sodium, salts.

The compositions according to the invention may take any form suitable for administration including forms suitable for oral, rectal or parenteral (including implant) use. For oral administration the compositions may take the form of, for example solutions, syrups or suspensions e.g. in aqueous buffer, or solid compositions such as tablets or capsules, prepared by conventional means. For parental use, the compositions may for example take a form suitable for injection, such as a suspension, solution or emulsion in an aqueous or oily vehicle optionally containing formulatory agents such as suspending, stabilising, solubilising and/or dispersing agents.

In the compositions according to the invention the concentration of active ingredient may be varied for example depending on the nature of the animal to be treated and the desired effect, but in general sufficient will be used to facilitate the administration of a dose of active ingredient in the range 0.01 to 0.2 mg/kg live weight/day.

The compositions according to the invention may be prepared by conventional means and in a further aspect of the invention we provide a process for the manufacture of a veterinary composition comprising bringing into association an aliquot amount of a recombinant polypeptide having porcine growth hormone activity selected from pGH(met 1-190) or pGH(4-190) and the veterinary acceptable salts thereof with one or more carriers acceptable for veterinary use.

Thus for example the recombinant polypeptide may be mixed or blended with, or suspended or dissolved in, a carrier as appropriate, using conventional techniques.

The plasmid expression vectors for use in the process according to the invention may be obtained using the methods described below. The methods generally describe in a first series of steps the preparation of plasmid vectors containing DNA sequences coding for polypeptides having porcine growth hormone activity, which are useful storage vehicles. A second series of steps illustrate the use of the storage vehicles to construct plasmid expression vectors for use in the process according to the invention.

The processes described are particularly useful for plasmid expression vectors capable of a high level of expression of pGH(met 1-190) and pGH(4-190), but are generally applicable for the preparation of vectors expressing other porcine growth hormone variants.

Thus according to a further aspect of the invention there is provided a process for the preparation of a recombinant DNA plasmid including a DNA sequence coding for a polypeptide having porcine growth hormone activity which process includes:

providing a DNA sequence coding for a polypeptide having porcine growth hormone activity; and a plasmid vector;

and ligating the DNA sequence and plasmid vector to deploy the DNA sequence within the plasmid vector.

The recombinant DNA plasmid vector so formed may include a complete copy of a porcine growth hormone polypeptide coding region, and may include a 3' untranslated sequence beyond the termination codon of the structural gene.

The DNA sequence coding for a polypeptide having porcine growth hormone activity may be derived from mRNA, i.e. as cDNA. The mRNA, e.g. polyadenylated mRNA, may be obtained from an appropriate tissue source; for instance, isolated from porcine pituitary tissue. Accordingly, in a further aspect of the present invention, there is provided a process for the preparation of a DNA sequence coding for a polypeptide having porcine growth hormone activity, which method includes:

obtaining mRNA coding for a porcine growth hormone polypeptide from porcine pituitary tissue, and preparing from said mRNA a cDNA sequence having first and second strands complementary to said mRNA.

The extraction of polyadenylated RNA from porcine pituitary tissue may be conducted utilising a guanidine thiocyanate treatment followed by a chromatographic extraction.

The step of preparing cDNA from mRNA according to this aspect of the 5 present invention may include:

annealing primer oligo-dT to the mRNA;

treating the mRNA with reverse transcriptase to form a first strand of CDNA;

treating the first strand of cDNA with a Klenow fragment of DNA-polymerase and subsequently with reverse transcriptase to form a second strand of DNA on the first strand;

and treating the product thereof to cleave the covalent link between the first and second strands.

The cleaving step may be undertaken with an appropriate enzyme for example nuclease-S1.

The plasmid vector for the cloning of the double stranded DNA may be of any suitable type, for example the plasmid vector pBR322. The cloning step may take any suitable form. The homopolymer tailing/annealing method may be used. In this case the plasmid expression vector may be modified to create overhanging 3' extensions. For example, pBR322 may be digested with the restriction endonuclease Pst 1. The plasmid vector pBR322 may also be tailed with approximately 15 nucleotides of guanidine residues.

Similarly, the DNA sequence may be tailed with cytosine residues 5 utilising terminal transferase.

In order to identify vectors containing pGH sequences, suitable host cells, e.g. *E. coli* may be transformed with the vectors, cells transformed with vectors containing inserted DNA sequences may be selected by appropriate means, e.g. resistance to antibiotics, and inserted pGH sequences identified by ability of vector DNA to hybridise with pGH-specific polynucleotide probes.

Accordingly, in a further aspect of the invention we provide recombinant DNA plasmids selected from pGH3, pGH4 and pGH29 as hereinafter specifically described. The plasmid pGH29 is particularly preferred. As discussed below, each of these plasmids includes a complete copy of the porcine growth hormone polypeptide coding region, extending past the 3' termination codon.

It will be understood, however, that whilst such recombinant DNA plasmids provide a useful storage vehicle for DNA sequences coding for polypeptides having porcine growth hormone activity, the vector requires additional prokaryotic host-compatible operator sequences to control and promote expression of such eukaryotic genes in prokaryotic host cells; i.e. the vector must be an expression vector which is compatible with prokaryotic host cells. Thus, the proper replication transcriptions and translation signals must be correctly arranged on the plasmid to ensure that the foreign gene will be properly expressed in the transformed cells and their progeny.

Accordingly in a further aspect of the invention there is provided a method of preparing a recombinant DNA plasmid expression vector including a DNA sequence coding for a polypeptide having porcine growth hormone activity and capable of being replicated, transcribed and translated in a unicellular organism which method includes:

providing a restricted plasmid expression vector, and a DNA sequence coding for a polypeptide having porcine growth hormone activity, or a portion thereof, said DNA sequence including a synthetic sequence at the 5' end thereof satisfying the regulatory requirements for replication transcription and translation in a unicellular organism; and ligating the DNA sequence into the plasmid expression vector in a position such that replication transcription and translation of said DNA sequence can occur.

The restricted plasmid expression vector according to this aspect of 5 the present invention may be of any suitable type. A dual-origin vector of the kind described in the specification of published British patent application GB 2136814A is preferred. A dual-origin vector has one origin of replication which is responsible for the stable maintenance of plasmid at low copy number whilst the other LO origin, replication of which is switched on by a change in temperature or other means, directs constitutive synthesis of cloned genes. Thus, induction of copy number amplification in large scale cultures is relatively cheap and simple.

A plasmid expression vector pMG197, a derivative of pMG411 (described in Gene, 1984 by Yarranton et al and in GB 2136814A) may be used as a starting material plasmid for preparing recombinant DNA plasmid expression vectors according to this aspect of the invention. pMG197 is a dual origin plasmid expressing met-Gastric Lipase enzyme from the trp promoter which has a Shine-Dalgarno (SD) sequence 14 base pairs upstream from the AUG start codon.

pMG197 may be modified to form a restricted plasmid expression vector, for example by deleting the EcoR1 site between the par locus and the c1857 sequences and by excluding the met-Gastric Lipase gene as a BglII-EcoR1 fragment.

A recombinant DNA plasmid expression vector according to this aspect of the invention may be prepared using a two step process.

Accordingly in a preferred embodiment of this aspect of the invention, wherein the said DNA sequence comprises a portion only of the DNA sequence coding for procine growth hormone consisting of a synthetic 5' end sequence and a 3' end sequence, the method further includes:

providing a further DNA sequence comprising the remainder of the sequence coding for porcine-growth hormone:

cleaving the said DNA sequence at a restriction site between the synthetic 5' end sequence and the 3' end sequence, and ligating the further DNA sequence into the restriction site.

Preferably one of two general types of oligonucleotides may be used as the synthetic 3' end sequence of the said DNA sequence. Thus two general types of oligonucleotides may be designed to replace the DNA coding for the first 17 amino acids (ending at the 3' ApaI Site) of the pGH coding sequence.

The first type of oligonucleotide, oligonucleotide met 1-17 includes a codon specifying methionine at position 1, followed by sequence coding for the first seventeen amino acids of porcine growth hormone. The codons chosen, whilst coding for the amino acids, preferably correspond to the most abundant tRNAs found within *E. coli.*

The second type of oligonucleotide, oligonucleotide met 4-17 was similarly designed but did not include DNA coding for the first three amino acids of pGH: PHE, PRO, ALA. Transcription from this gene would start at the codon for methionine, the amino acid normally occupying the fourth position in the pGH polypeptide chain. The base sequences of the two types of oligonucleotides may be chosen within the constraints of the genetic code. In order to maximise the gene expression it is found preferable to select host preferred codons which are expressed at high level in *E. coli*. In addition computer analysis may be performed to search for and remove regions of potential secondary structure within the ribosome binding site of the messenger RNA. As part of this second exercise G-C base pairs may be substituted where possible with A-T base pairs. Genes for the highly expressed outer membrane proteins of *E. coli* comprise extremely A/T rich promoter regions. These regions, responsible for the control of transcription, bind the DNA-dependent RNA polymerase which copies the messenger RNA from the DNA template.

Furthermore, 5' sequence dictating translation efficiency is also found to be extremely A/T rich. The area between the Shine-Dalgarno sequence and the initiating ATG is believed to effect an instability on secondary structure thereby facilitating ribosome binding and subsequent translation along the message.

Examples of specific oligonucleotides which may be synthesised are as follows:

5' GATCTATGTTTCCAGCTATGC-
CACTTTCTTCTCTCTGTTCGCTAACGCTGTTCTTCGGGCC
3'(SEQ ID NO:1)

3' ATACAAAGGTCGATACGGTGAAAGAA-
GAGACAAGCGATTGCGACAAGAAGC 5'(SEQ ID NO:2)

met 1 to 17 oligonucleotides

5' GATCTATGCCACTTTCTTCTCTGT-
TCGCTAACGCTGTTCTTCGGGCC 3'(SEQ ID NO:3)

3' ATACGGTGAAAGAAGAGACAAGCGAT-
TGCGACAAGAAGG 5'(SEQ ID NO:4)

met 4 to 17 oligonucleotides

Accordingly in a further aspect of the present invention there is provided a plasmid expression vector including a DNA sequence coding for a polypeptide having porcine growth hormone activity, or a portion thereof and wherein the DNA sequence has a segment at the 5' end replaced by a synthetic sequence satisfying the regulatory requirements for replication transcription and translation in a unicellular organism.

The regulatory sequence may be selected from met 1-17 oligonucleotides and met 4-17 oligonucleotides as described above including the specific sequences mentioned.

Thus, for use with the restricted pMG197, described above, which excludes the BglII-EcoRI fragment, the synthetic oligonucleotide sequence may be ligated to an ApaI-EcoRI fragment of the DNA sequence derived from pGH29. This comprises DNA coding for amino acids 88 to 190 of pGH. The present invention accordingly provides in a still further aspect an intermediate plasmid expression vector selected from pMG933 and pMG934 as hereinafter specifically described. These intermediate plasmid expression vectors incorporate the synthetic met 1-17 oligonucleotides and met 4-17 oligonucleotides specifically described above respectively.

The synthetic sequence so formed may then be joined to the restricted expression vector (BglII-EcoR1).

The remaining fragment of the DNA sequence coding for porcine growth hormone which comprises a mid-section of DNA coding for amino acids 18-87 may then be included. A small ApaI-ApaI fragment may be isolated from an ApaI digest of the plasmid expression vector pGH29. The intermediate plasmid expression vector pMG933 or pMG934 may be cleaved at the ApaI restriction site and the ApaI-ApaI fragment cloned thereinto to yield expression vectors pMG935 and pMG936 respectively.

The recombinant plasmid expression vector so formed may be used to transform suitable host cells and the transformed host cells cultured to express porcine growth hormone polypeptides as described above, Samples of *E. coli* containing the plasmids and plasmid expression vectors specifically described herein are maintained in the Bunge (Australia) Pty. Ltd. Cell Collection, 87–89, Flemington Road, North Helbourne, Victoria, Australia.

The present invention will now be more fully described with reference to the accompanying Examples. It should be understood, however, that this example is illustrative only and should not be taken in any way as a restriction on the generality of the invention as described above.

Example 1

PREPARATION OF pGH cDNA

Growth hormone comprises a major fraction of porcine pituitary proteins, and the messenger RNA for pGH is likewise abundant, constituting some 25% of total mRNA (John H. Nilson et al, J. Biol. Chem. 258 (1983)). The strategy for obtaining cDNA clones encoding pGH was to use the entire mRNA population as a template for cDNA synthesis and to select from the population of cDNA clones those containing the porcine GH gene. In summary this involved:

(1) Extraction of Poly A containing RNA from adult pig pituitary using the guanidium thiocyanate method and chromatography on oligo (dT) cellulose.

(2) Synthesis of cDNA using both reverse transcriptase and the Klenow fragment of DNA-Polymerase 1.

(3) Cloning into *E. coli* HB101 recA- using Pst 1 restricted pBR322 and the homopolymer annealing method.

ISOLATION OF PITUITARY RNA

Frozen pig anterior pituitary glands were homogenised in a glass teflon homogeniser in 0.5 ml of 5M guanidine thiocyanate, 1% sarkosyl, 20 mM EDTA, 1% (v/v) 2-mercaptoethanol, 50 mM Tris-HCl, pH 7.0. The homogenate was brought to a final volume of about 3.5 ml with additional homogenisation buffer, layered over 1.2 ml of 5.7M CsCl containing 0.1M EDTA, pH 7.0 in a Spinco SW 50.1 centrifuge tube, and centrifuged for 17 hr at 36,000 rpm at 20° C. The supernatant was carefully removed with a Pasteur pipette and the RNA pellet dissolved in 0.5 ml of sterile $H_2O$ at room temperature followed by a 30 second incubation at 60. The RNA was precipitated twice at −20° by the addition of 0.1 volumes of 2M potassium acetate, pH 5 and 2.5 volumes of 95% ethanol (modified from Chingwin et al. Biochem. 18, 5294 (1979)).

SELECTION OF POLY(A)+RNA

Messenger RNA, or more precisely polyadenylated RNA can be isolated from a mixture of RNA species by chromatography on oligo-dt (dT-cellulose). Oligo-dt (dT-cellulose), Type 77, was purchased from Pharmacia. The resin was equilibrated in sterile loading buffer (20 mM Tris-HCl (pH7.6), 0.5M NaCl, 1 mM EDTA, 0.1% SDS) and a 1.0 ml column poured. The column was washed three times with each of a) sterile $H_2O$, b) 0.1M NaOH/5mM EDTA and c) sterile $H_2O$ (or until the column effluent pH was less than 8). Five volumes of sterile loading buffer were then passed through the column. The RNA was prepared by suspension in sterile $H_2O$ and heat-treatment at 65° C. for 5 minutes. An equal volume of 2×loading buffer was added to the RNA sample, which was then allowed to cool to room temperature before application to the column. Column flow-through was collected, heated to 65° C. for 5 minutes, cooled and re-applied to the column. The column was then washed with 5–10 column volumes of loading buffer, followed by 4 column volumes of 20 mM Tris-HCl (pH 7.6), 0.1M NaCl, 1 mM EDTA, 0.1% SDS. The polyadenylated RNA was eluted with 2–3 column-volumes of sterile 10 mM Tris-HCl (pH 7.5), 1 mM EDTA, 0.05% SDS and precipitated with 3M sodium acetate and ethanol. The pellet was resuspended in sterile $H_2O$ and stored at −70° C. Elution of polyadenylated DNA was followed by reading the optical density at 260 nm.

SYNTHESIS OF COPY DNA

Following selection, polyadenylated mRNA was converted to double-stranded cDNA and inserted into a bacterial plasmid (as per "A Laboratory Guide to Molecular Cloning" - Maniatis et al (1982) Cold Spring Harbour Laboratories). Briefly, this involved synthesis of the first strand with reverse transcriptase (RNA-dependent DNA polymerase); removal of the RNA template by alkaline digestion; synthesis of the second strand with both reverse transcriptase and DNA polymerase 1 (the Klenow fragment); and finally, removal of the hairpin loop (covalently joining the first and second strands) by enzymatic digestion with nuclease-S1.

Synthesis of the first strand

Before the enzymatic synthesis of the cDNA was undertaken, the integrity of the poly(A)+RNA was checked by (agarose-formaldehyde) gel electrophoresis. Synthesis was initiated by mixing approximately 10 ug of polyadenylated mRNA, 50pmoles of each of the nucleotides (dGTP, dCTP, dATP, dGTP), and 1 ul of 100 nM methylmercuric hydroxide. This mixture was held at room temperature for 10 minutes to enhance the yield of full-length mRNA template. Prior to the addition of the reverse transcriptase, 2 ul of 700 mM 2-mercaptoethanol was added to sequester the mercury ions which are known to inhibit the action of reverse transcriptase. 1 ul of RNasin (approximately 25 units) was also added to inhibit any degradation of the RNA. The mixture was held for a further 15 minutes at room temperature after which, 40 units (2 ul) of reverse transcriptase were added and incubation continued at 42° C. for 3 hours. The reaction was stopped by the addition of 2 ul 0.5M EDTA (pH 8.0), and 25 ul of 150 nM NaOH. The mRNA template was hydrolysed during a 1 hour incubation at 65° C. The DNA was precipitated in 3M sodium acetate and absolute EtOH at −70° C., spun for 10 minutes in an Eppendorf centrifuge and the pellet dried.

SECOND-STRAND SYNTHESIS

To ensure that full-length copies of DNA are made, second strand synthesis from the first strand template is achieved using DNA polymerase 1 in conjunction with reverse transcriptase. As both enzymes stall at different points along the template, their concurrent use increases the chance of reading through the entire length of sequence.

The dried 1st strand cDNA pellet was resuspended in 50ul of sterile $H_2O$ and an equal volume of 2×2nd-strand buffer (0.2M HEPES (pH 6.9); 20 mM $MgCl_2$; 5 mM dithiothreitol; 0.14 KCl; 1 mM DTTP; 1 mM dCTP; 1 mM dATP; 1 mM dGTP) was added. The reaction was initiated by the addition of 40 units of the Klenow fragment of DNA-polymerase 1 and held at 15° C. for 20 hours. After 20 hours had elapsed, the DNA-polymerase 1 was inactivated by the addition of 2.0 ul of 0.5M EDTA (EDTA chelates the divalent magnesium ions which are crucial components of an active enzyme complex). The sample was extracted with equal volumes of phenol/chloroform and the ds cDNA was separated from the unincorporated dNTPs by chromatography on Sephadex G-50. The DNA was precipitated with 3M sodium acetate and absolute ethanol at −70° C., dried and then resuspended in 40 ul of sterile water, 20 ul of the cDNA was taken and to it was added, 5 ul 1M Tris-HCl (pH 8.3), 7 ul 1M KCl, 2 ul 250 mM $MgCl_2$, 25 ul of 20 mM (dATP, dTTP, dGTP, dCTP), 2ul 700 mM 2-mercaptoethanol, 7 ul $H_2O$ and 2 ul (40 units) reverse transcriptase. The reaction mixture was incubated at 42° C. for 1 hour and then stopped by the addition of 2.0 ul 0.5M EDTA. The mixture was extracted with an equal volume of phenol and chloroform, followed by chromatography on Sephadex C-50 to remove the unincorporated dNTPa. The DNA was precipitated with 3M sodium acetate and ethanol at −70° C.

Digestion with Nuclease-Sl

At the conclusion of first and second strand synthesis, both strands are covalently bound by a single-stranded loop. This is easily removed by digestion with nuclease-Sl. Approximately 0.5 ug of double-stranded cDNA was suspended in 50 ul of 1 mM Tris-HCl )(pH 7.6) 0.1 mM EDTA. 10 ul of 10×nuclease-Sl buffer (2M NaCL, 0.5M sodium acetate (pH 4.5), 10 mM $ZnSO_4$, 5% glycerol) was added and the reaction mixture made up to 100 ul with sterile water. The reaction was initiated with the addition of 5 units of nuclease-Sl, and continued at 37° C. for 30 minutes, after which time, the enzyme was inactivated by 11 ml of 0.5 mM EDTA.

Digestion with nuclease-Si generates double-stranded sequences with differing overhang sequence. The fragments are made blunt ended by repair with the Klenow fragment of *E. coli* DNA polymerase 1 (2 units) and the four deoxyribonucleotides (25 mM stock solution). The DNA is separated from unincorporated nucleotides by chromatography on Sephadex G-50.

Cloning double-stranded DNA

The pGH cDNA is homopolymer tailed with cytosine residues by terminal transferase. Enzyme concentration and time were determined for a chain-length of approximately 15 nucleotides. Similarly, the plasmid vector pBR322 was digested with the restriction endonuclease Pst 1 (which creates overhanging 3' extensions) and tailed with approximately 15 nucleotides of guanidine residues.

Double-stranded CDNA and linearised plasmid DNA were treated as follows:

DNA, suspended in 55ul of sterile water, was added to an equal volume of 2×tailing buffer (0.4M potassium cacodylate, 50 mM Tris-HCl (pH 6.9), 4 mM dithiothreitol, 1 mM $CoCl_2$, 2 ml ($^3H$)dGTP (for the plasmid DNA) or 2 ml ($^3H$)dCTP (for the cDNA), 500 ug/ml BSA). A 10 ul aliquot was used to determine the duration required for the addition of approximately fifteen nucleotides. The remaining linear plasmid DNA was incubated for 10 minutes at 37° C. The reaction was stopped by chilling to 0° C. followed by the addition of 10 ul of 0.5M EDTA (pH8). After an extraction in equal volumes of phenol and chloroform, homopolymer-tailed DNA was separated from low-molecular weight contaminants by chromatography on Sephadex G-100 (equilibrated in 1×annealing buffer: 1M NaCl, 0.1M Tris.Cl (pH 7.8), 1 mM EDTA).

The vector DNA and pGH cDNA were mixed and precipitated with 3M sodium acetate and ethanol at −70° C. The dried DNA was resuspended in 50 ul of ligase buffer (30 mM Tris-HCl (pH8), 4 mM $MgCl_2$ 1.2 ml EDTA, 1.0 mM dithiothreitol and 50 ug/ml BSA). The reaction was catalysed by 2 ul T4 DNA ligase (Pharmacia) and held at 10° C. for 16 hours. A 25 ul aliquot of the reaction mixture was transformed into *E. coli* HB101 as described below:

100 ul of L Broth (1% yeast extract, 1% tryptone, 0.5% NaCl) was innoculated with 1 ml of an overnight bacterial culture (*E. coli*, HE101). The cells were grown at 37° C. for 3 hours on a shaking platform. After 3 hours, the cells were chilled and spun in a bench centrifuge for 5 minutes at 4° C.; the supernatant was discarded. The cells were resuspended in 50 ml of ice-cold, sterile solution of 50 mM CaCl and 10 mM Tris-HCl (pH 8) and held in ice for 15 minutes. The cells were then harvested by spinning in a bench centrifuge, resuspended in 6.5 ml of an ice-cold, sterile solution of 50 ml $CaCl_2$ and 10 mM Tris-HCl (pH 8) and 0.2 ml aliquots dispensed into prechilled tubes. The cells were stored to 4° C. for 24 hours to increase the efficiency of transformation. After 24 hours had elapsed, plasmid DNA resuspended in TE buffer (10 mM Tris-HCl (pH 8), 1 mM EDTA) was added to the cells, mixed and held on ice for 30 minutes. The cells and DNA were then heat-shocked at 42° C. for 2 minutes. 1.0 ml of L Broth was added to each tube and incubated at 37° C. for 30 minutes. During this period the bacteria recover and begin to express antibiotic resistance. After 30 minutes, 10 ul of serial dilutions were spread-plated on agar plates supplemented with tetracycline or ampicillin.

Whilst all bacterial cells harbouring the intact plasmid, pBR322, grow on ampicillin and tetracycline, bacterial containing the recombinant plasmid with the pGH cDNA cloned into the Pst 1 site of pBR322 grow only on tetracycline as the ampicillin resistance is lost by this recombination. Colonies which grew only on tetracycline, were further screened with a single-stranded, radio labelled cDNA probe synthesised from total pig pituitary poly A+ RNA (pig growth hormone message accounts for approximately 25% of the polyadenylated RNA). On this basis, the more highly labelled colonies were selected. Tetracycline resistant colonies were plated onto nitrocellulose filter discs in an orderly array. The cell walls were lysed under alkaline conditions to release the DNA which was then fixed to the filters by heat treatment at 80° C. for 2 hours. Radiolabelled total pig pituitary cDNA was incubated with the filters at 37° C. for 16 hours. The filters were washed in 2×SSC, dried and autoradiographed. Positive colonies were isolated and subjected to restriction analysis with a number of four and six base cutting enzymes. A partial restriction map was compared to published sequence data (FIG. 1) and pGH clones were selected. Of the three positive clones (pGH3, pGH4, and pGH29), plasmid pGH29 (FIG. 2) was found to be best suited for further manipulation. pGH29 included a complete copy of the porcine growth hormone cDNA, extending past the 3' stop codon.

CLONING INTO THE DUAL ORIGIN VECTOR, pMG197

1. Synthesis of oligonucleotides

Prior to ligating the porcine growth hormone cDNA into the plasmid, pMG197 (FIG. 3) it was necessary to modify the vector to include appropriate prokaryotic regulatory sequences which could be fused to the 5' end of the eukaryotic gene, pGH cDNA.

In general, cDNA of genomic eukaryotic DNA does not carry the appropriate regulatory signals which (in the case of endogenous prokaryotic DNA) would ensure efficient transcription and translation of the gene. This shortcoming can be overcome by the engineering of synthetic oligonucleotides which can be tailored to suit preferred codon usage of the host strain and include unique restriction sites.

Two sets of oligonucleotides designed to be ligated to the 5' ApaI restriction site of the pGH gene were required to express both pGH met (1-190) and pGH (4-190) in the dual origin plasmid used. These were synthesised by phosphotriester chemistry (Patel, et al, (1982) Nucleic Acids Res. 10, 5605-5620).

5' GATCTATGTTTCCAGCTATGC-
CACTTTCTTCTCTGTTCGCTAACGCTGTTCTTCGGGCC 3'
(SEQ ID NO:1)

3' ATACAAAGGTCGATACGGTGAAAGAA-
GAGACAAGCGATTGCGACAAGAAGC 5' (SEQ ID NO:2)

met 1 to 17 oligonucleotides

5' GATCTATGCCACTTTCTTCTCTGT-
TCGCTAACGCTGTTCTTCGGGCC 3' (SEQ ID NO:3)

3' ATACGGTGAAAGAAGAGACAAGCGAT-
TGAGACAAGAAGC 5' (SEQ ID NO:4)

met 4 to 17 oligonucleotides

2. Strategy for inserting pGH cDNA into pMG197

Vectors for expression of hybrid porcine growth hormone polypeptides were constructed as follows:

The respective synthetic oligonucleotides (BglII-ApaI) were kinased, ligated and then restricted with ApaI and BglII. The correct fragments were isolated from an agarose gel and then ligated to ApaI-EcoRI fragments (coding for amino acids 88-190) derived from pGH29. The linearised fragment was joined to the BglII-EcoRI restricted expression vector (Bgl2-EcoRI), transformed into E. coli strain DH1, amplified and selected. This intermediate contained both the 5' and 3' ends of the pGH gene but lacked the mid-section coding for amino acids 18-87 of pGH. A small ApaI-ApaI fragment 5 (approximately 200 bp, coding for amino acids 18-87) was isolated from an ApaI digest of pGH29 and cloned into the ApaI site of the intermediate vector thereby completing the porcine growth hormone gene (FIG. 4). The correct orientation of the plasmid was identified which gave the two expression plasmids pMG935 (met 1 to 190 pGH) and pMG936 (4 to 190 pGH). The plasmids were transformed into E. coli DH1 host strain and the constructions were checked following amplication in ampicillin supplemented L-broth media by restriction analysis and sequencing by the method of Sanger.

3. DNA Sequence of PGH gene

The sequencing was carried out by the Sanger dideoxy method using restriction fragments of the pGH plasmids subcloned into M13 phage. Only one of the pGH plasmids, pMG936 (pGH 4 to 190) was fully sequenced, as the majority of the pGH sequence was common to both constructs. The other pGH plasmid, pMG935 (pGH met 1 to 190) was therefore only sequenced at the 5' end of the pGH gene, through the junction fragments.

Analysis of the data

Two restriction digests were required to obtain all the overlapping fragments necessary for sequencing both strands of DNA. The gene is located between the HpaI and EcoRI restriction sites (see FIG. 5). Digest "1" was a triple digest using Hpa 1, Sma 1 and EcoRI which gave two pGH gene fragments of about 470 bp and about 300 bp. Digest "2" was a double digest Hind 111 and Apa 1 and gave three pGH-related fragments of about 220 bp, 1000 bp and 1500 bp. All these fragments were purified from gels and Si nuclease treated to generate blunt fragments. The fragments were then cloned into the bacteriophage M13 vector, which had previously been digested with EcoRV and phosphatase treated. Each clone was sequenced to obtain 5 up to 300 bases of sequence. Overlapping restriction fragments were chosen so as to obtain the complete DNA sequence on both strands.

The sequence found agrees with that published except for one base change of an A TO a G at position 446 (FIG. 6). This change however does not alter the protein sequence, as both codons (GAA or GAG) give glutamic acid. This difference in DNA sequence probably relfects allelic variation in the pGH gene.

The same restriction digests were carried out on pMG935, but only the fragments marked  and * in FIG. 5 were cloned and sequenced; the fragments marked * were sequenced because they cover the different 5' end of the pGH (met 1 to 190) gene, whilst the fragments marked  were sequenced to confirm that the base change found in pMG936 was also present in pMG935. The sequence data assembled was exactly as expected, including the base change at position 446.

Optimisation of Ribosome Binding Sites and Selection of Best Plasmids

Various DNA manipulations have been reported to increase the level of accumulation of heterologous protein products in E. coli. Most of these modifications seek to increase the amount of gene expression and focus on the 5' non-coding region of the gene. In addition to changes to the promoter sequences, changes can also be made which alter the structure of the messenger RNA. These alterations affect how the ribosone interacts with the messenger RNA and change the rate at which translation of the messenger RNA into protein is initiated. In particular, varying the distance between the sequence complementary to the 3' end of 16S a ribosomal RNA (the Shine-Delgarno sequence) and the ATG codon at the start of the structural gene frequently has marked effects on gene expression (Roberts et al, P.N.A.S., USA, 76, 760–764, 1979). A fuller description of procedures which may lead to the maximisation of gene expression can be found in Old and Primrose, Principles of Gene Manipulation, 3rd Ed., pp 138–182, 1985).

The Shine-Dalgarno to ATG (SD to ATG) distance in E. coli genes which are highly expressed is commonly between 6 and 12 bases. The optimal sequence is not easy to predict, since the conformation of the messenger RNA also determines the expression level and this conformation is determined by hydrogen bonding between sequences on the messenger RNA both upstream and downstream of the ribosome binding site. This includes sequences within the structural gene of the protein.

The most effective way of determining the best sequence is to create a series of related plasmids and screen these for the highest level of protein accumulation.

Modification of the ribosome binding site

The original plasmids expressing pGH (met 1 to 190) and pGH (4 to 190) were specially designed to facilitate the construction of such a family of plasmids. Both originally had a SD to ATG distance of 14 base pairs. The synthetic oligonucleotides used to construct pMG935 and pMG936 contained a sequence which has unique restriction enzyme cleavage sites for the enzymes Cla 1 and BglII: (SEQ ID NO:6)

SHINE-DALGARNO SEQUENCE        FIRST CODON OF pGH

```
 1 2 3 4 5 6 7 8 9 10 11 12 13 14
A A G G G T A T C G A T A G A T C T ATG 3'

T T C C C A T A G C T A T C T A G A T A C 5'

Cla 1           BglII
```

These enzymes cleave the double stranded DNA of the expression plasmid asymetrically, leaving single stranded regions. These can be either removed (using S1 nuclease) or filled in (using the Klenow fragment of DNA polymerase 1). The treated DNA can then be ligated to give a series of plasmid molecules with SD to ATG of between 5 and 12 base pairs. A single digest followed by filling in would extend the SD-ATG; hence filling in reactions have only been used when two enzyme digests were performed. N.B. Optimisation was performed on plasmids pMG935 and pMG936 respectively; it was found that plasmids pMG935 (met 1 to 190) and pMG936 (4 to 190) contained a redundant EcoRl fragment from the lipase coding sequence. This was removed, giving pMG939 and pMG940 respectively; the plasmids have not had their pGH genes or expression sequences altered.

Figure 7:
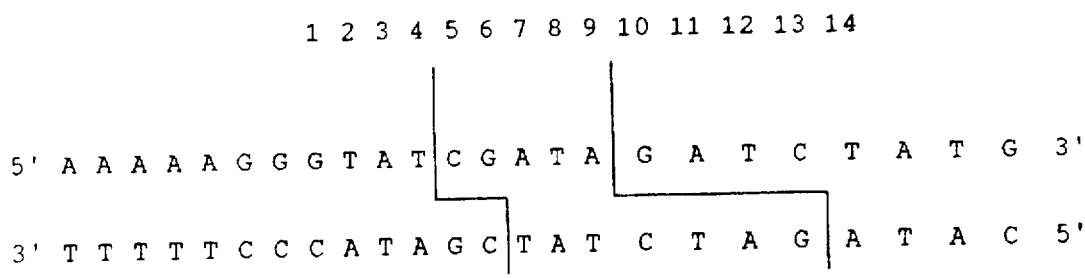
FIG. 7 lists the combined enzyme treatments for altering the length of the Shine-Dalgarno to ATG sequence and the expected result.

A complete list of all the combinations of enzyme treatments performed, and their expected products is shown in FIG. 7.

Filling of the single stranded extension at the cut site by DNA polymerase 1 filling in is usually accurate, but S1 nuclease digestion is much more difficult to control. S1 nuclease is a single strand specific enzyme which works in both directions. When a single stranded end has been removed, the remaining double stranded end should not be digested. However, since the strands are held together only by hydrogen bonds, there is a tendency for the terminal bases to be digested as the hydrogen bonds break and re-form in thermodynamic equilibrium. The consequence of this is that extra residues may be removed, especially when the terminal base pair is A:T, since this pair has only two hydrogen bonds compared with the three bonds in a G:C pair.

FIGS. 8 and 9 illustrated a programme of plasmid modification using either pMG 939 or pMG 940 to obtain other plasmids according to the invention which contain different SD to ATG distances to the parent plasmids.

N-Terminal Amino Acid Sequence of Recombinant pGH (met 1 to 190)

A loading of 5 nmole recombinant pGH (met 1 to 190) was used to carry out 24 cycles of degradation in an AB1 protein sequencer. The result was consistent with the previously published pGH sequence (plus Met at the N-terminus): i.e. 15 Met-Phe-Pro-Ala-Met-Pro-Leu-Ser-Ser-Leu-Phe-Ala-Asn-Ala-Val-Leu-Arg -Ala-Gln-X-Gln-Leu. (X=uncertain) (SEQ ID NO:7).

Some estimate of "preview", an indicator of N-terminal proteolysis, could be made from the sizes of PTH-methionine peaks in early cycle analyses when PTH-met background was negligible, and from the sizes of PTH-Leu peaks with background substraction. The estimate is that less than 2% of the pGH (met 1 to 190) molecules are missing one amino acid residue. Another estimate, from PTH-alanine peaks without background. substraction gave approximately 5% molecules missing one amino acid but this is probably an overestimate due to 5 lack of background subtraction.

Protein Expression

Small-scale cultures of pMG935/E. coli DH1 and pMG936/E. coli DH1 were grown at 30° C. for 1.5 hours. The amplification of plasmid copy number and gene expression was induced by shifting the temperature to 42° C. Samples were removed at hourly time points, before and after induction, and analysed by electrophoresis on SDS-polyacrylamide gels (SDS-PAGE). After staining with Coomassie Blue, significant levels of a heat inducible protein of the correct apparent molecular weight for both pGH met (1-190) and pGH (4-190) were found. pGH protein levels reached maximum levels seven hours after induction. These bands were confirmed to be growth hormone by Western blot analysis of an identical SDS-PAGE gel using a pGH-specific monoclonal antibody 21-51.

Biological Activity

Porcine growth hormone derived from recombinant plasmids in E. coli has been compared to natural porcine growth hormone isolated from the pituitaries of pigs. Equivalent amounts of the protein were injected into hypophysectomized rats (Long-Evans) over a four day period. Twenty-four hours after the last injection the rats were sacrificed and the right tibia isolated. The bone was cleaned and split at the proximal end in the midsagittal plane. The ipiphyseal cartilage can be distinguished from surrounding bone following staining with silver nitrate. The results are expressed as percentage increases:

|  | CONTROLS | | RECOMBINANTS | |
|---|---|---|---|---|
|  | −ve | +ve | 4-190 | 1-190 |
| mean | 1.7 | 4.4 | 3.9 | 4.1 |
| % increase | 0 | 158% | 129% | 141% |

−ve control: hypophysectomized rat + buffer
+ve control: hypophysectomized rat + natural GH
4-190: recombinant GL from pMG936
1-190: recombinant GH from pMG93S Finally, it is to be understood that various other modifications and/or alterations may be made without departing from the spirit of the present invention as outlined herein.

EXAMPLE 2

Preparation of pGH(met 1-190) and pGH(4 190)
(a) Fermentation

Six liters of medium containing glycerol (15g/l), $(NH_4)_2SO_4$ (5.0 g/l), $NaN_2PO_4$ 6.24(g/l), and trace elements solution (20 ml/l) was sterilised in a 10l fermenter.

The medium was inoculated with 200 ml of a shake flask culture of E. coli cells containing pMG935 and grown at 34° C. with aeration and stirring. The pH was controlled at 7.0 with ammonium hydroxide 10 solution. Sterile glycerol was added at intervals to maintain an excess throughout the fermentation.

After ten hours, pGH production was induced by raising the culture temperature to 42° C. for 10 minutes and then cooling to 38° C. This temperature was held for a further six hours.

The final biomass was 26 g dry cell weight/l and phase contrast microscopy showed inclusion bodies within the cells. The cells were harvested by centrifugation for 15 minutes at 5000 rpm in 11 bottles in a Beckman J6 centrifuge, and stored at −13° C. until required.

A second fermentation was carried out under identical conditions except that E. coli cells containing pMG936 were used.

(b) Homogenisation of cells, recovery and solubilisation of pGH, purification and refolding (i) Cell Homogenisation Samples of cell paste [E. coli pMG935 and pMG936 prepared according to Section (a)] were suspended in 390 ml of 50 ml sodium phosphate buffer at pH7, and containing 5 ml EDTA, 0.5M NaCl, 0.1 mM PMSF.

The cells were lysed using a French pressure cell (1 pass at 1200 psi). Approx. 1 mg DNase I was added to each suspension in order to digest DNA released on cell lysis.

(ii) Recovery of Insoluble Denatured pGH by Centrifugation pGH (met 1-190)

The cell homogenate was centrifuged at 5000 rpm for 35 minutes, to recover inclusion bodies in a partially purified form. The pellet (13 g) was resuspended in 160 ml sodium phosphate buffer pH7, and containing 5 mM EDTA, 0.5M NaCl, 0.1 mM PMSF and centrifuged again. The supernatants were discarded after SDS-PAGE which indicated that pGH was present in the pellet.

pGH (4-190)

The cell homogenate was centrifuged at 12,000 rpm for 5 minutes. The pellet (10 g) was washed several times with Triton-X-100 and the supernatants discarded.

(iii) Solubilisation and Renaturation of pGH

Each pellet containing pGH inclusion bodies and prepared in Section (ii) was solubilised in 50 mM Tris pH 8.9, 7M guanidine HCl, 1 mM EDTA, 100 mM 2-mercaptoethanol (7 ml/g pellet). After clarification 28 ml of each solution was chromatographed on a Sephacryl S300 column (2.2×85cm) which had been equilibrated with 50 mM Tris pH8.9, 7M guanidine HCl, 1 mM EDTA, 50 mM 2-mercaptoethanol. In the case of pGH (4 to 190) two runs were carried out. The eluate from each column was collected in fractions and monitored by absorbance at 280 nm. Aliquots of the column fractions were dialysed into 25 ml Tris-HCl pH7, 8M urea, 0.1% (v/v) 2-mercaptoethanol and analysed by SDS-PAGE. Fractions containing the required polypeptides were pooled and each pool was dialysed against 4 changes of a 20 fold excess of 15 ml Tris HCl pH9, 7M urea, 50 mM 2-mercaptoethanol. The retentate (50 ml of pGH met 1 to 190 or 180 ml of pGH 4 to 190) was adusted to pH 7 with 1M HCl before applying to a DEAE cellulose (DE 52) column (4.4×11 cm). The ion exchange matrix was equilibrated with 15 ml Tris-HCl pH 7, 7.5M urea, 50 mM 2-mercaptoethanol. A peak or protein was eluted from the column by 2 bed volumes of equilibration buffer. This peak was shown to contain pGH by SDS-PAGE. Gel scanning showed pGHmet (met 1 to 190) was approximately 95% pure whereas pGH(4–190) was only 45% pure, probably because of overloading of the DE52 column. This material was therefore purified further by a second DE52 step.

Pooled fractions from ion exchange chromatography were dialysed against 3 changes of 25 fold excess of 25 nm Tris pH 10., 1% (wv) mannitol using visking tubing. Each protein was refolded by this slow removal of denaturant and reducing agent.

The dialysed fractions were then divided into 2 ml aliquots, frozen in liquid nitrogen, and stored at −70° C. The protein concentration of the fractions was measured using the Bio-Rad protein assay with absorbance read at 595nm. Approximately 100 mg refolded porcine growth hormone (met 1 to 190) was obtained from 13 g (wet weight) of cell paste. 60 mg of refolded 4 to 190 pGH was recovered from 26 g (wet weight) cell paste.

Further analysis was carried out to authenticate the products:

(iv) FPLC was used to show that the recombinant pGH preparations were of the correct molecular wight, and did not contain any aggregates such as dimers. A Superose 12 column (30×1.0 cm) was euqilibrated with 100 mM Tris-HCl pH 8.0 and calibrated with a range of known molecular weight standards. The following elution times were obtained with pGH:

| authentic pGH | 27.7 min |
|---|---|
| rec pGH (met 1 to 190) | 27.5 min |
| rec pGH (4 to 190) | 27.0 min |
| mixed injection | 27.2 min |

A single peak observed in each case. The ability of the column to resolve pGH dimers was demonstrated using ovalbumin, which has the same molecular weight as a pGH dimer, i.e. 44,000 daltons.

Molecular weight assignments of FPLC peak fractions were confirmed by SDS-PAGE.

(v) To confirm that the 22 Kd material was pGH related, Western blotting analysis was carried out using a pGH-specific mouse monoclonal antibody 21–51. A 157% reduced SDS polyacrylamide gel of each recombinant polypeptide and authentic standard was electroeluted onto a nitrocellulose filter and probed with the pGH mouse monoclonal antibody. This was then probed with rabbit antimouse polyclonal antibody, and detected with $^{125}$I labelled protein A. The resulting autoradiograph showed binding to the 22 Kd band. The recombinant materials were at least as pure as the authentic standard by this criterion.

(vi) Radioreceptor binding was investigated to obtain in vitro evidence for biological activity of pGH (met 1 to 190).

Authentic pGH was $^{125}$I labelled, and incubated overnight with pregnant rabbit liver membranes. Binding was measured by centrifuging the receptors and counting the pellet in a gamma counter. Displacement of label by cold authentic pGH was dose dependent. Recombinant pGH (met 1 to 190) was also shown to displace the $^{125}$I pGH indicating that the recombinant polypeptide is able to compete with authentic pGH for the receptor sites.

We claim:

1. A process for the production of a recombinant polypeptide having porcine growth hormone activity, said process comprising:
   (a) providing a dual-origin host-vector expression system comprising (i) a recombinant plasmid expression vector selected from the group consisting of pMG935, pMG936, pMG939 and pMG940 which encode a recombinant polypeptide which retains procine growth hormone activity, wherein said vector is replicated, transcribed and translated in a unicellular organism, and (ii) a unicellular organism;
   (b) introducing said recombinant plasmid expression vector into said unicellular organism by a method selected from the group consisting of transformation, transduction and transfection;
   (c) culturing said organism having said recombinant plasmid expression vector introduced therein; and
   (d) expressing said recombinant polypeptide having porcine growth hormone activity.

2. The process of claim 1, wherein said recombinant plasmid expression vector encodes a recombinant polypeptide selected from the group consisting of pGH(met 1-190) and pGH(4-190).

3. The process of claim 1, wherein said unicellular organism is a strain of *E. coli*.

4. The process of claim 1, wherein said unicellular organism is *E. coli* DH1.

5. A process for the production of a recombinant polypeptide having porcine growth hormone activity, said process comprising:
   (a) providing a dual-origin host-vector expression system comprising (i) a recombinant plasmid expression vector selected from the group consisting of pMG935, pMG936, pMG939 and pMG940 which encode a recombinant polypeptide which retains porcine growth hormone activity, wherein said vector is replicated, transcribed and translated in a unicellular organism and (ii) a unicellular organism;
   (b) introducing said recombinant plasmid expression vector into said unicellular organism by a method selected from the group consisting of transformation, transduction and transfection;
   (c) culturing said organism having said recombinant plasmid expression vector introduced therein;
   (d) expressing said recombinant polypeptide having porcine growth hormone activity as an insoluble aggregate;
   (e) isolating said insoluble aggregate produced in step (d);
   (f) solubilizing said insoluble aggregate; and
   (g) recovering said recombinant polypeptide having porcine growth hormone activity from said solubilized aggregate.

6. The process of claim 5, wherein said recombinant plasmid expression vector encodes a recombinant polypeptide selected from the group consisting of pGH(met 1-190) and pGH(4-190).

7. The process of claim 5, wherein said unicellular organism is a strain of *E. coli*.

8. The process of claim 5, wherein said unicellular organism is *E. coli* DH1.

9. A process for the production of a veterinary composition comprising a recombinant polypeptide having porcine growth hormone activity comprising the process of claim 5, and further including the step of:

(h) combining said recovered recombinant polypeptide having porcine growth hormone activity with at least one carrier acceptable for veterinary use to form a veterinary composition.

* * * * *